United States Patent [19]

Anghaie et al.

[11] Patent Number: 4,870,669
[45] Date of Patent: Sep. 26, 1989

[54] GAMMA RAY FLAW DETECTION SYSTEM

[75] Inventors: Samim Anghaie; Nils J. Diaz, both of Gainesville, Fla.

[73] Assignee: Florida Nuclear Associates, Inc., Gainesville, Fla.

[21] Appl. No.: 44,718

[22] Filed: May 1, 1987

[51] Int. Cl.⁴ .................................................. G01N 23/20
[52] U.S. Cl. .................................................. 378/87; 378/58
[58] Field of Search ............... 378/6, 58, 86, 87, 901; 364/414

[56] References Cited

U.S. PATENT DOCUMENTS

| | | | |
|---|---|---|---|
| 3,949,210 | 4/1976 | Eichinger et al. | 250/336.1 |
| 4,090,074 | 5/1978 | Watt et al. | 250/336.1 |
| 4,121,098 | 10/1978 | Jagoutz et al. | 250/336.1 |
| 4,423,522 | 12/1983 | Harding | 378/6 |
| 4,538,290 | 8/1985 | Nakamura | 378/86 |
| 4,608,635 | 8/1986 | Osterholm | 378/6 |

FOREIGN PATENT DOCUMENTS 2461877  7/1976  Fed. Rep. of Germany ........ 378/87

Primary Examiner—Craig E. Church
Attorney, Agent, or Firm—Fleit, Jacobson, Cohn, Price, Holman & Stern

[57] ABSTRACT

A collimated beam of gamma radiation is applied to a test object under non-destructive examination to produce a scattered gamma radiation field within which detectors are positioned to provide radiation energy level data of the field. Such measurement data is processed by comparison with reference data from a flawless object to provide differential scatter gamma spectra. The differential spectra are transformed by spatial-/energy data processing to extract accurate location and size data with respect to any flaws present in the test object.

5 Claims, 4 Drawing Sheets

GAMMA RAY FLAW DETECTION SYSTEM

BACKGROUND OF THE INVENTION

This invention relates to the non-destructive examination of material for the presence of flaws, and more particularly to the detection of flaws by use of gamma radiation.

Nondestructive inspection or examination of various industrial materials by use of radiation techniques, is already well-known. For example, ultrasonic inspection methods have been utilized for detection and measurement of structural flaws associated with nuclear reactor vessels and components thereof such as the Zircaloy tubes of the nuclear reactor fuel rods. However, certain questions have arisen in regard to the reliability and accuracy of such non-destructive inspection methods. Thus, the need for a more reliable, although non-destructive, inspection system still exists not only for nuclear reactor installations but also for industrial materials in general of critical importance to safety in areas such as power plant and defense installations, and in space exploration related environments. Thus, non-destructive and reliable inspection of vessels, pipes, shafts and turbine blades for cracks, voids, discontinuities and other defects or flaws in both near, far and mid-surface ranges remains a problem for which better solutions are being constantly sought.

The use of high energy photon type of radiation applied as a collimated bean to a variety of liquid and solid materials for examination thereof by imaging is already known. For example, the use of x-rays or Gamma rays to analyze coal or coke by measurement of radiation scatter is disclosed in U.S. Pat. No. 4,090,074 to Watt et al. Generally, such prior gamma or x-ray analyzing systems include geometrical arrangements for restricting material penetration by the radiation or scatter thereof, as disclosed for example in U.S. Pat. No. 4,423,522 to Harding, in order to accommodate the radiation detector. Such systems are therefore unable to provide sufficiently accurate information with respect to small sized voids, cracks or flaws in the materials being analyzed.

X-ray examination systems utilizing multi-channeled, peak voltage discrimination techniques to detect, size and locate defects is generally known as disclosed for example, in U.S. Pat. No. 4,121,098 to Jagoutz et al. Such prior non-destructive material analyzing systems are preferable to the use of the aforementioned ultrasonic examination methods wherein surface flaws may totally block transmission of ultrasonic waves. However, the x-ray analyzing method as disclosed in the Jagoutz patent is incapable of being reliably applied to a wide variety of materials and for detecting flaws located at different depths within the material being examined.

The use of gamma ray energy sensitive detectors having superior energy resolution characteristics, are generally known as disclosed for example in U.S. Pat. No. 3,949,210 to Eichinger et al. Such radiation detectors are utilized for gamma ray spectroscopy without any disclosed relationship to techniques for detecting, locating and sizing material flaws.

It is therefore an important object of the present invention to provide a non-destructive material inspection system through which flaws may not only be detected from scatter radiation but to also provide reliable and accurate data from which such flaws may be located and the sizes thereof determined.

An additional object of the present invention in accordance with the foregoing object is to provide a non-destructive material inspection or examination system capable of providing reliable and accurate data with respect to the location and size of material flaws regardless of the depth range within which the flaws are located within the material.

Yet other objects of the present invention in accordance with the foregoing objects is to provide a non-destructive material inspection system providing more reliable and accurate measurement of material flaws in a variety of different environments including, but not limited to, industrial, laboratory, power plant and aircraft sites where safety is of critical concern.

SUMMARY OF THE INVENTION

In accordance with the present invention, gamma radiation in a narrow collimated bean is utilized during non-destructive examination of materials, without refraction or reflection, for location and measurement of microscopic density discontinuities and other such flaws in the material. The total field of scattered gamma radiation emerging from the examined material being irradiated, avoiding prior art radiation restricting arrangements is analyzed through a semi-conductor detector array having a characteristically high energy resolution to extract the desired information from the examined material within a wide range of optical thickness. The desired information to be extracted includes accurate location and size data pertaining to flaws detected from energy density distribution profiles of the scattered radiation field extending from the material being examined, such profiles representing measurements resulting from intersection of the examined material along the axis of the incident radiation beam. The scattered radiation field profiles are compared with reference profile data obtained from flawless material to obtain a differential gamma scattering spectrum transformed by system geometry data into a space dependent spectrum in order to minimize the introduction of detection error because of the effects of multiple radiation scattering.

It is a significant discovery of the present invention that the differential gamma scattering spectrum aforementioned provides accurate and reliable data from which flaw size and location may be determined despite the multiple scattering effect and without scatter radiation restriction. According to one embodiment of the invention, such differential spectrum is obtained with respect to the axis of a gamma radiation beam extending through a chordal portion of the object under examination by means of a detector located within the scattered radiation field in a position to view the gamma radiation illuminated chordal portion. The signal output of the detector is processed to provide a profile of radiation energy distribution within the scattered radiation field along the incident radiation beam axis. A reference profile of a flawless object is subtracted from the profile obtained from the flawed object under examination to provide the differential gamma scattering spectrum having pulse-shaped portions representing the detected flaws. Accumulation, processing and readout of such peak-shaped differential spectra provides information on the location of the flaws and from the area enclosed by the pulse portions, data on the size of the flaws is provided. Such data processing of the differential, peak-shaped spectrum is based on certain mathematical relationships between the differential density distribution of scattered radiation energy along the irradiated chord of the test object under examination and the density of the test object as well as a multiple scattering error factor associated with the detection system. For test objects having very small flaws, the differential value of the multiple scattering factor was found to be negligible so that the differential density distribution becomes almost a direct function of the average density of the test object. The discovery that the detection error effects of multiple scattering become smaller as the size of the flaws becomes smaller, provides an unexpectedly attractive feature to the system of the present invention in connection with the detection, location and measurement of relatively small flaws in large and massive test objects. Thus, from known mathematical relationships associated with the radiation scattering kinematics of the detection system, precise location of the flaws may be determined from the differential spectra aforementioned.

In accordance with one embodiment of the invention the outputs of the detectors are processed by known signal processing electronics and collected in histogram memories of a multi-channel analyzer within which a pulse height analysis is executed under control of the software program of a computer with which the multi-channel analyzer is interfaced. The computer program transforms the data in accordance with an energy/spatial data conversion program and executes a comparison operation to generate the differential gamma scattering spectra from which data is extracted and processed to provide a readout of flaw location and size.

In accordance with other embodiments of the invention, the data processing computer has a multi-mode operational program associated therewith. One operational mode is selected in response detection of relatively small flaws to calculate flaw size as a substantially direct function of the differential density distribution of the test object since the multiple scattering error factor is negligible under such conditions as hereinbefore pointed out. A second operational mode is selected in response to detection of larger flaws, in which case a more complex calculation is performed by the computer based on both the differential density distribution and the multiple scattering factor. In the latter operational modes, location of the flaws is based on a mathematical calculation involving polar scattering angle relationships between the detector and the respective peak energy levels of each differential, peak-shaped spectrum. According to yet another operational mode, initial detection of flaws is achieved by a primary off-beam detection operation providing an initial gamma scattering spectrum. Such operation is repeated with incremental translation of the test object relative to the gamma ray beam until the beam passes through the test object. The differential spectrum data then obtained will provide the flaw location and size information as aforementioned. The flaw location and size data may be readout by the data processing system associated with the invention in the form of visual displays providing for example, differential scattering imaging and tomography or data plotting by means of a printer.

BRIEF DESCRIPTION OF DRAWING FIGURES

The foregoing objects, features and advantages of the invention, as well as others, will become apparent from the following detailed description given by way of example to be read in connection with the accompanying drawings, wherein.

DETAILED DESCRIPTION OF PREFERRED EMBODIMENTS

Figure 1:
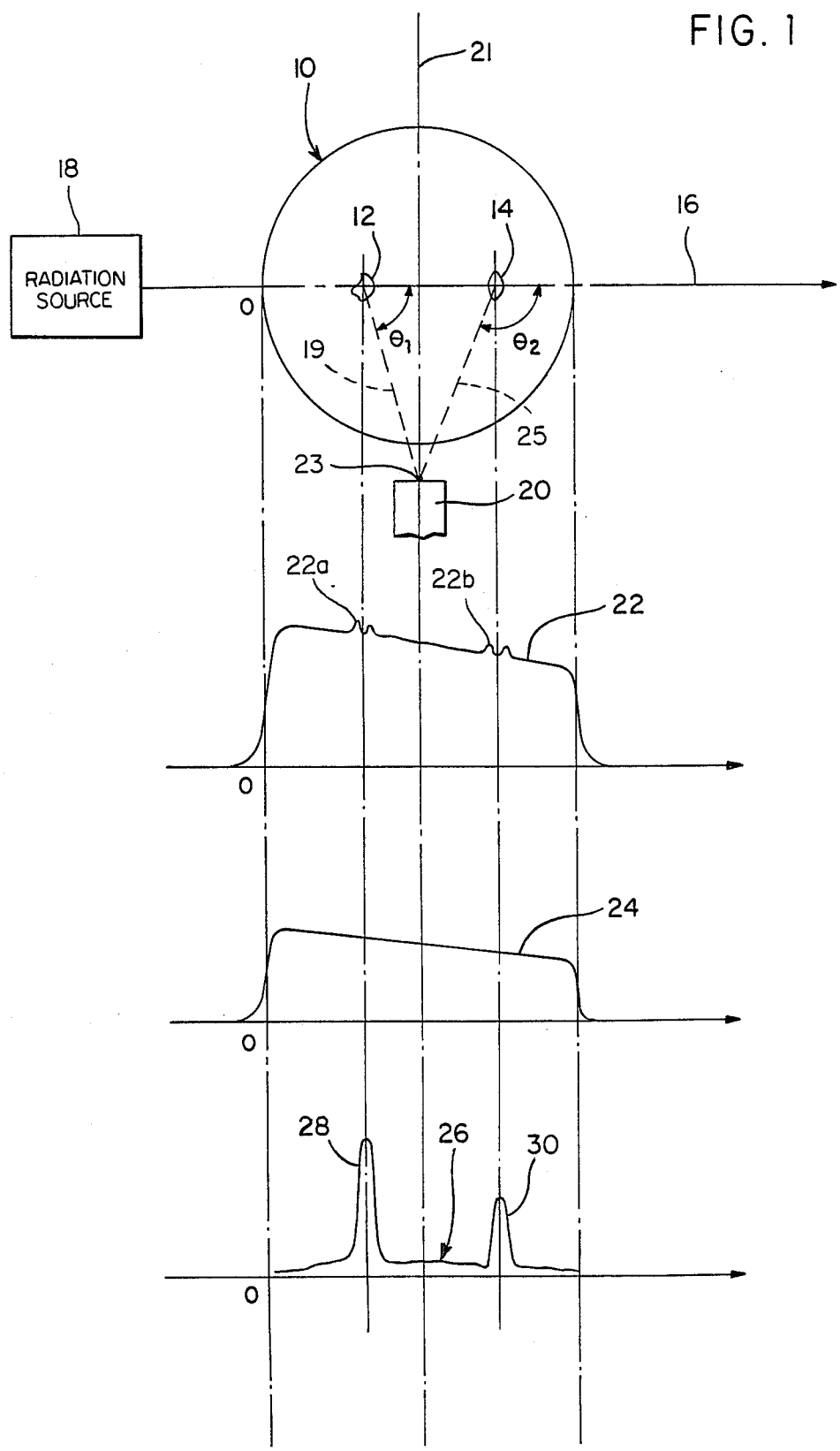
FIG. 1 is a schematic and graphical illustration of radiation energy levels and spatial relationships associated with the present invention.

Referring now to the drawings in detail, FIG. 1 illustrates test material in the form of a solid cylindrical object 10 being examined in accordance with the present invention for the existence of possible defects or flaws, such as the voids 12 and 14 shown. The flaws 12 and 14 are located in spaced relation along a chordal portion of the test object 10 coinciding with the axis 16 of a collimated gamma ray beam emitted from a monoenergetic source 18 of gamma rays. As a result of the illumination or irradiation of the test object 10 by the beam of gamma rays, scattered gamma radiation emerges from the test object to form a scattered radiation flux field within which a detector 20 is located in accordance with the present invention as shown in FIG. 1. The detector is of a semi-conductor type known in the art, consisting for example of a large silicon or germanium diode of the p-n or p-i-n type in a reverse bias mode. At a suitable temperature, the barrier created at the semi-conductor junction associated with such detectors, reduces the leakage current to acceptable low values so that the field in which the detector is disposed, will cause collection of charge carriers liberated by the ionizing radiation of the field. The gamma radiation emitting source 18 may be a commonly available radioisotope source.

The detector 20 as diagramed in FIG. 1 is aligned along an axis 21 at right angles to the beam detection axis 16 to establish polar scattering angles $\theta_1$ and $\theta_2$ between lines 19 and 25 extending from a common detection point 23 on axis 21 of the detector to flaw locations and the beam axis 16 where it intersects such flaw locations at the flaws 12 and 14.

By means of the energy level measurements made of the scattered radiation flux field by the detector 20, a scattering gamma radiation field profile of energy density distribution is obtained and compared with a similar reference profile obtained by detection of the scattered radiation emerging from a flawless object similarly irradiated by a narrow collimated beam of gamma rays. A differential gamma scattering spectrum profile is thereby obtained by subtraction of the reference profile from the measured test profile. The differential gamma scattering spectrum in accordance with the present invention provides the basis for obtaining reliable and accurate data on the size of the flaws 12 and 14 detected in the test object 10 with reference to FIG. 1. Such flaw size data is obtained because of the mathematical relationship between the differential gamma scattering spectrum δD(E) and the differential density distribution δρ along their irradiated chordal portion of the test object under investigation as set forth in the following mathematical expression:

$$\delta\rho = (\lambda a)/F \cdot \delta D(E) - \rho_r\{B_r(E) - B(E)\},$$

where $\rho_r$ is the reference object density, $B_r(E)$ and $B(E)$ are the multiple scattering factors for the reference and flawed object spectra, respectively.

The relationships expressed in the foregoing equation are graphically illustrated in FIG. 1 showing curve 22 representing the scattered radiation emerging from the flawed test object 10 along the chordal portion of the test object on which the flaws 12 and 14 are located. Pulse formations 22a and 22b on the curve 22 represent the flaws. Such flaw indicating pulse formations are not present, however, in a similar reference curve 24 obtained in connection with the flawless reference object as aforementioned. Thus, a differential radiation spectrum profile curve is 26 obtained by subtraction of curve 24 from 22 and includes pulse portions 28 and 30 at locations corresponding to the flaw indicating portions 22a and 22b of the curve 22. The areas under the pulse portions 28 and 30 of the differential profile curve 26, are respectively proportional to the size of the flaws 12 and 14 corresponding to the flaw size data aforementioned.

The location of the flaws 12 and 14 as depicted in FIG. 1, may be determined from the scattering angles $\theta_1$ and $\theta_2$ and from the peak energy levels $E_1$ and $E_2$ of the respective pulse portions 28 and 30 of the differential spectrum curve 26, in accordance with the following mathematical expressions:

$$\theta_1 = \cos^{-1}[1 - M_0C^2(1/E_1 - 1/E_0)]$$

$$\theta_2 = \cos^{-1}[1 - M_0C^2(1/E_2 - 1/E_0)],$$

where $E_0$ is the peak energy level of the incident gamma ray beam and $M_0C^2$ is the electron rest mass energy value. Thus, based on the foregoing mathematical expressions of the energy/spatial relationship, accurate location of the detected flaws may be determined in accordance with the present invention.

Figure 2:
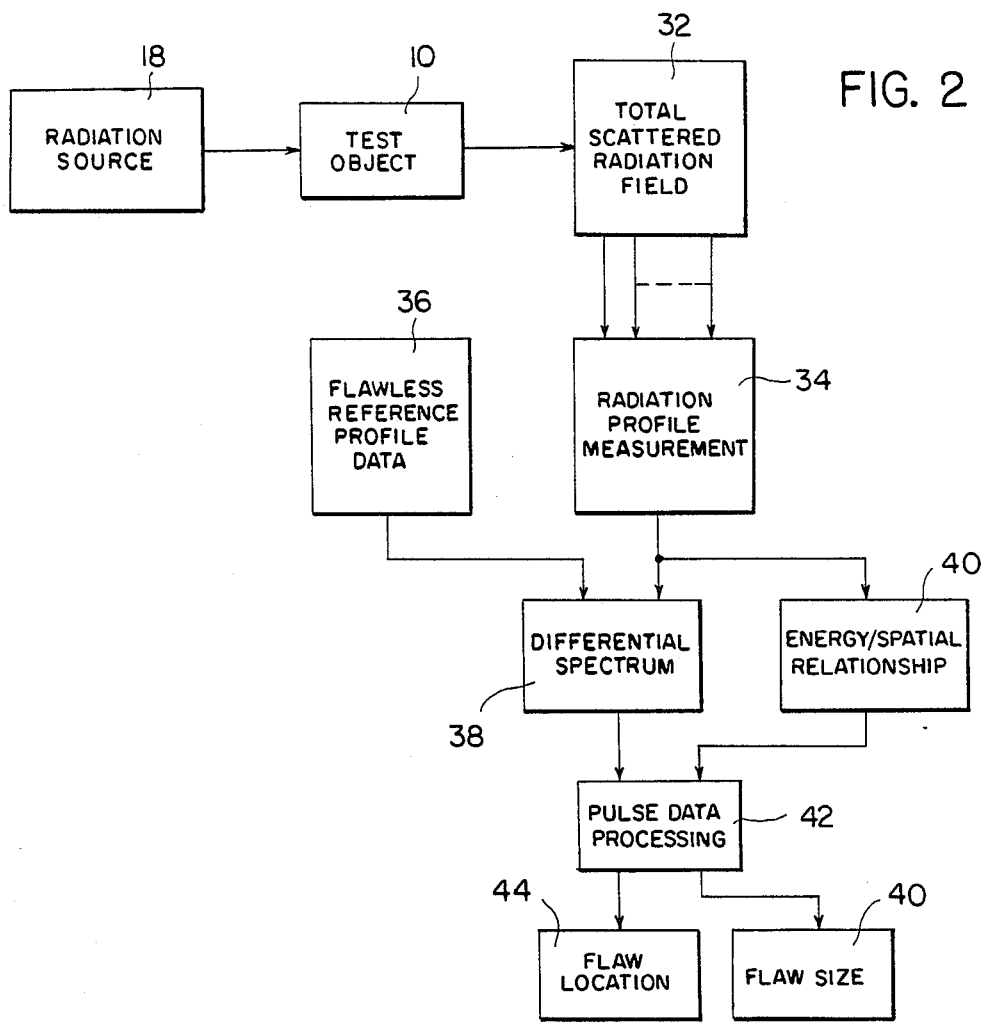
FIG. 2 is a functional block diagram schematically illustrating the basic method associated with the present invention.
Figure 3:
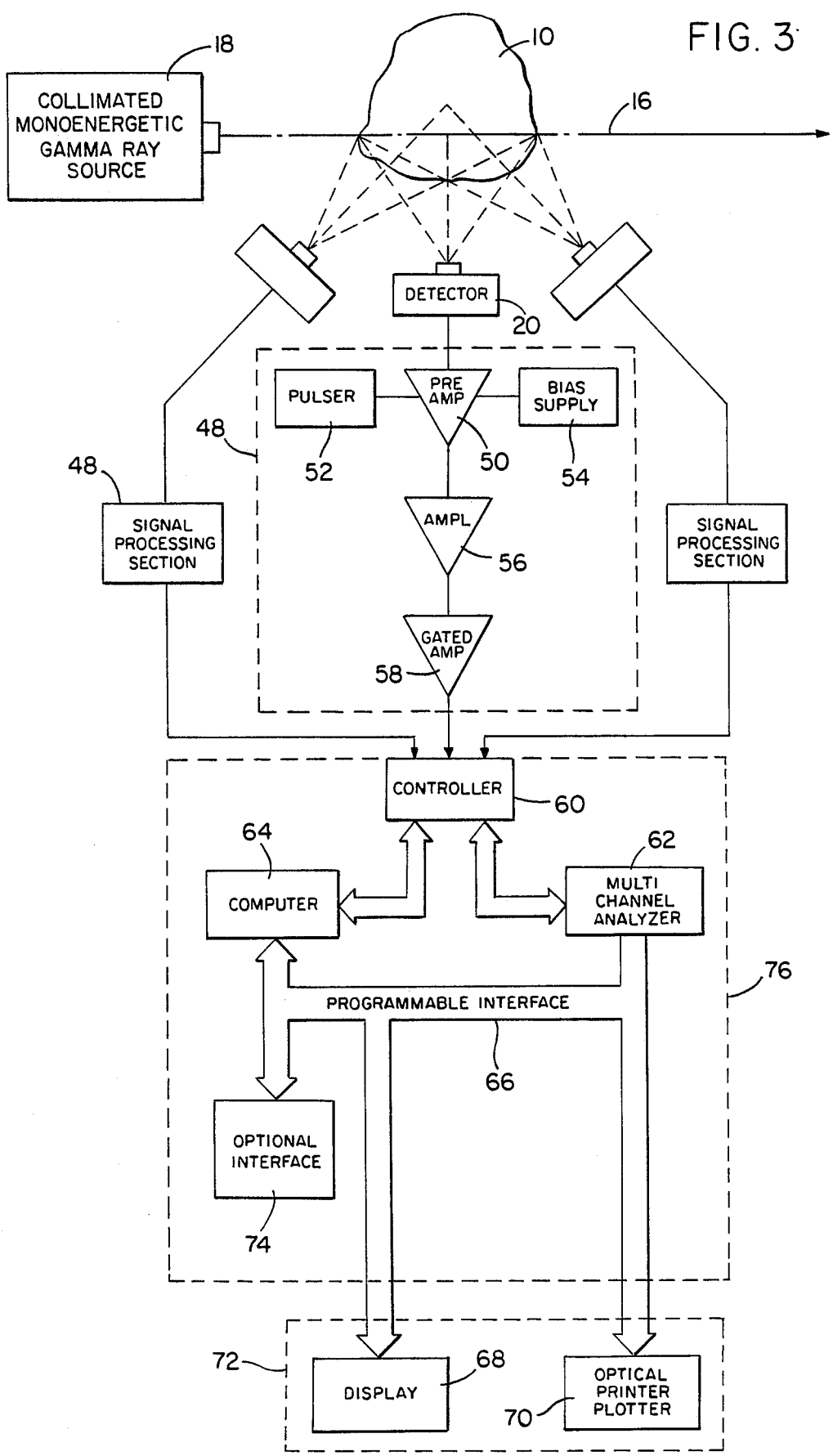
FIG. 3 is schematic circuit diagram illustrating a hardware arrangement in accordance with one embodiment of the present invention.

The method of detecting and determining the location and size of flaws in a test object as hereinbefore described, may be carried out in accordance with one embodiment of the invention by a signal and data processing system as schematically depicted in the functional block diagram of FIG. 2. As depicted in FIG. 2, the test object 10 is irradiated by the radiation source 18 to establish a total scattered radiation field 32 from which a plurality of profiles are obtained by energy level measurements in section 34 through a plurality of detectors 20 as aforementioned. The signal outputs of the profile measuring section 34 are compared with a flawless reference profile stored in a data source 36 to provide corresponding differential spectra stored in memory section 38. From the outputs of the profile measuring section 34, energy/spatial relationship calculations are performed in section 40 in order to appropriately transform the differential spectrum readout of memory section 38 within a pulse data processing section 42. The pulse data processing section 42 will thereby produce readouts of flaw location at 44 and flaw size at 46. FIG. 3 more specifically illustrates an arrangement of hardware for performing the functional operations depicted in FIG. 2.

Referring now to FIG. 3 in detail, it will be observed that a plurality of high resolution semi-conductor detectors 20 are utilized such as the three shown by way of example in order to provide the energy field profile measurement data in the form of electrical signals generated by the detectors. The signal output of each detector is accordingly fed to a signal processing section 48 formed by electronic components already well known in the art, the details of which form no part of the present invention. Each signal processing section by way of example may include a preamplifier 50 to which a pulser 52 and bias supply 54 are connected. The signal output of the preamplifier is further amplified by amplifier 56 and transmitted to a system controller 60 through an amplifier 58 which may be gated pursuant to a program hereinafter described, to prevent transmission of signals and data processing thereof until the axis 16 of the radiations beam intersects a flaw in the test object. The controller 60 which forms part of a data processing section 76, is operatively interconnected with a multi-channel analyzer 62 and a computer 64 by programmable interface 66. The multi-channel analyzer 62 is thereby programmed to accumulate and store spectral data transmitted from the radiation detectors 20 through the signal processing sections 48 and controller 60. The computer 64 processes and transforms the data in accordance with an energy/spatial transformation program to rearrange the channel numbers addressing scattering sites through the multi-channel analyzer 62. The foregoing programmed interrelationship established by interface 66 also controls the readout of data fed to a visual display 68 and an optical/printer plotter 70 associated with a system readout section 72. An optional interface 74 may also be connected to the interface 66 and form part of the data processing section 76 of the system. The foregoing components of the data processing section 76 are also per se well known in the art, the details of which form no part of the present invention.

Figure 4:
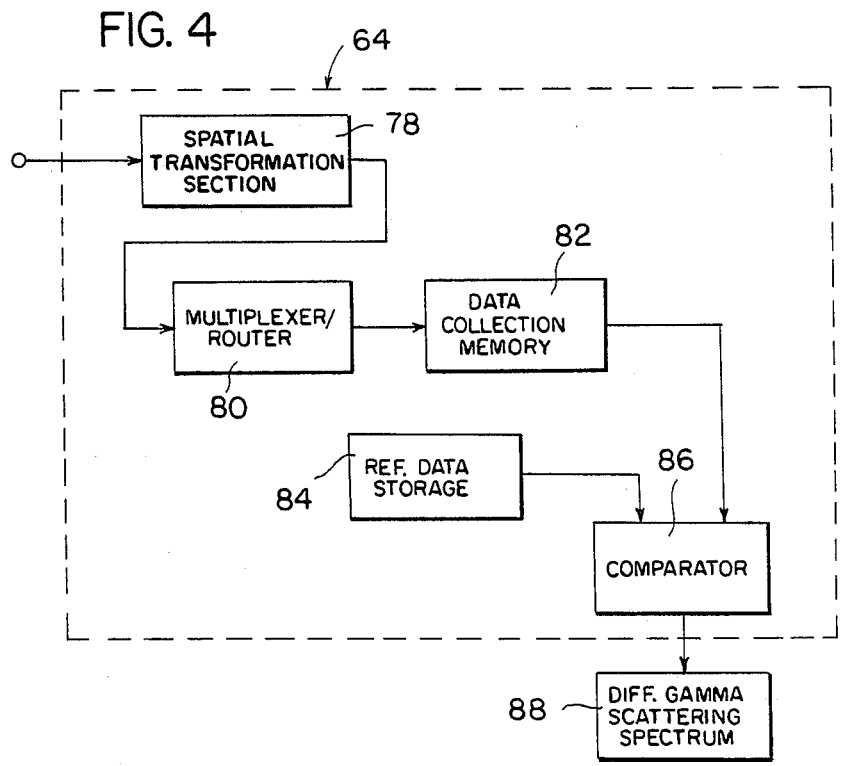
FIG. 4 is a block diagram of the functional components associated with the computer section shown in FIG. 3.

As diagramed in FIG. 4, the computer portion 64 of the data processing section 76 in response to pulse inputs from the controller 60 performs spatial transformation as indicated by block 78 with respect to such inputs in order to feed transformed multiple input data from the radiation field detectors to a multiplexer/router 80. Each individual input is fed by the multiplexer/router 80 to a section of a data collection memory 82 selected by routing bits. Such collected data from memory 82 is compared with the collected data from previously recorded reference data storage 84 by a comparator 86, the output of which is converted into the differential gamma scattering spectra through output section 88. In this manner, the computer portion 64 processes the input data to provide readout of flaw location and size in accordance with the method hereinbefore described.

The multi-channel analyzer 72 as indicated with respect to FIG. 3, performs a pulse/height analysis operation to accumulate a spectrum of the frequency distribution of the heights of a sequence of input pulses. The desired spectrum is accumulated by measuring the amplitude of each input, converting it to a number or channel address that is proportional to the pulse height and storing such information in a memory composed of individual channels. The count value of each channel is equal to the total number of pulses processed, the amplitude of which correspond to the channel number. The number of pulses is proportional to the number of photons scattered from the irradiated chordal portion of the test object, which in turn is proportional to the mass density distribution ($\rho$) in accordance with a mathematical relationship, pursuant to which the multi-channel analyzer is programmed, as follows:

$$\rho = \left[ \frac{\lambda e}{F(E) \cdot B(E)} \right] D(E),$$

where $\lambda e$ is the total exponential optical path, F(E) is an installational factor, B(E) is the multiple scattering factor and D(E) is the detected scatter gamma ray spectrum. Accordingly, the multi-channel analyzer 62 functions to accumulate and store data acquired from the detectors in a histogram memory so as to present such data for display and store it for construction of the differential gamma scattering spectra as aforementioned.

Figure 5:
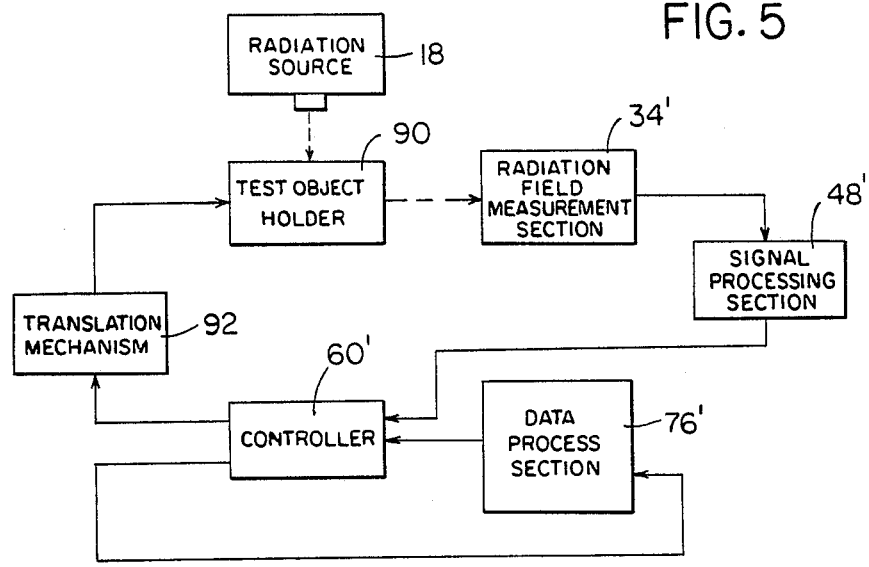
FIG. 5 is a block diagram of a hardware arrangement in accordance with another embodiment of the invention.

FIG. 5 illustrates by means of a functional block diagram, a modification on the signal and data processing system as hereinbefore described. In this embodiment of the invention, the test object is mounted on a movable holder 90 adapted to be incrementally displaced or rotated in vertical or horizontal directions by means of a translating mechanism 92. The translating mechanism is controlled by a system controller 60' through which data is fed to a data processing section 76', the data being derived from the detectors in the radiation field measurement section 34' from which signal outputs are processed through section 48' similar to the arrangement hereinbefore described with respect to FIG. 3. The modified system of FIG. 5, however, has a multi-mode operational program pursuant to which the amplifier 58 is gated as aforementioned, such program being depicted in the program flow chart of FIG. 6. A flaw detection operation is initiated as indicated by start 94 to begin radiation emission from the source as indicated at 96. The radiation field measurement section will then determine whether the gamma ray beam has passed through a flaw in the test object so as to make a decision as indicated at 98 of the program chart. If the beam passes through a flaw in the test object, a profile measurement operation ensures as indicated at 100 followed by a pulse data processing operation producing the differential scatter spectra as indicated at 102 corresponding, for example, to the graphical curve 26 in FIG. 1 and a spatial determination as indicated at 104. If the differential scatter spectra indicates a relatively small flaw reflected, for example, by intensity comparison with statistical noise, a decision is made as indicated at 106 to perform a flaw location and size calculation under one operational mode as indicated at 108, based on the aforementioned mathematical expression in which the object density and multiple scattering factor terms $\rho_r\{f(E) - B(E)\}$, are negligible. A more complex mathematical determination of flaw location and size under a second operational mode is performed as indicated at 110 if the flaw size is large relative to the test object.

Figure 6:
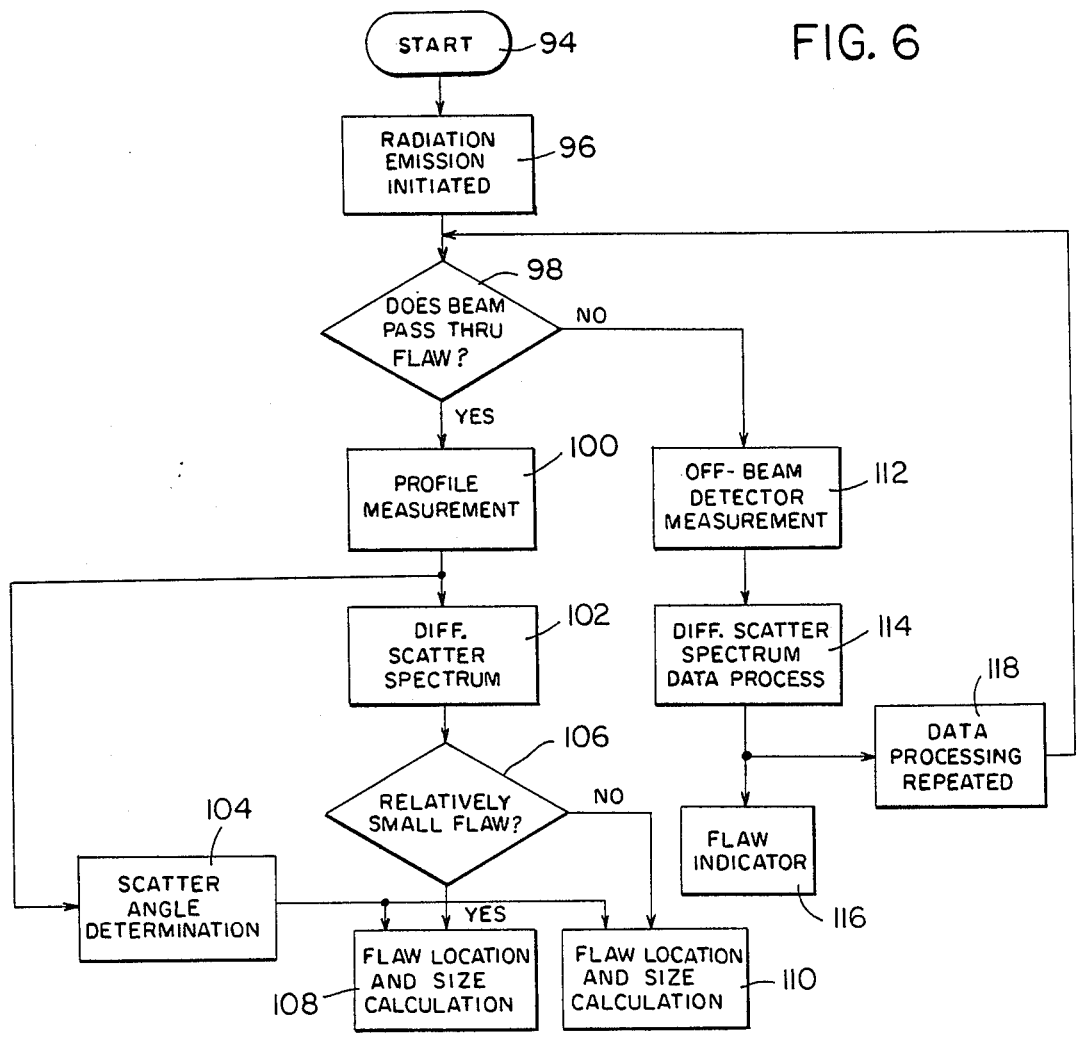
FIG. 6 is an operational program chart associated with the embodiment of the invention shown in FIG. 5.

In the event the incident beam of gamma radiation does not pass through any flow in the object, as determined at the decision block 98 in FIG. 6, the radiation field measurement section performs an off-beam detector operation as indicated at 112. In this regard, it should be appreciated that even under off-beam conditions total scattered radiation field measurement will provide some indication of object flaw such as a broad hump shaped peak at the low energy end of the differential spectra as compared to the sharp pulse indications of the differential spectra curve 26 in FIG. 1. The data processing section will therefore also perform its operation producing the differential scatter spectrum as indicated at block 114 in FIG. 6, under off-beam conditions, to provide flaw indication as indicated at 116 under such off-beam conditions. Since such off-beam flaw indication is not suitable for providing accurate flaw location and size data, it will initiate a repeated data processing operation as indicated at program block 118 through the profile measurement section after incremental displacement has been imparted to the test object holder. Thus, the off-beam signal measurement and data processing loop depicted in FIG. 6 will be repeated until the beam passes through a flaw in the the test object enabling determination of flaw location and size at 108 and 110 in FIG. 6 in accordance with the criteria and formulae hereinbefore set forth with respect to flaw location and size as graphically depicted in FIG. 1.

The foregoing is considered as illustrative only of the principles of the invention. Further, since numerous modifications and changes will readily occur to those skilled in the art, it is not desired to limit the invention to the exact construction and operation shown and described and accordingly, all suitable modifications and equivalents may be resorted to, falling within the scope of the invention.

What is claimed is:

1. In a system for non-destructive examination of a test object by irradiation thereof from a monoenergetic source emitting a collimated beam of radiation and detection of scattered radiation emerging from the irradiated test object within a measurement field to provide scattered radiation density distribution profiles of the field from measurement of energy levels therein, a method of analyzing the detection of flaws in said irradiated test object, including the steps of: comparing the radiation density distribution profiles with a reference profile corresponding to measured energy levels of scattered radiation emerging from an irradiated flawless object to provide differential spectra of the field; determining spatial relationships of the measured energy levels in the field relative to said beam of radiation; and extracting location and size data of the flaws in the test object from the differential spectra by data transformation thereof in accordance with said determined spatial relationships, said radiation density distribution profiles being formed by accumulation of data on the measured energy levels from which data the reference profile is subtracted during said step of comparing to establish the differential spectra, said spatial relationships being determined by correlation of the measured energy levels and scattering angles between the beam of radiation and lines extending therefrom at flaw locations to a common radiation detection point, said step of extracting the size data of the flaws including measuring the areas under pulse portions of the differential spectra respectively corresponding to peak values of the measured energy levels, said measured areas being substantially proportional to the size of the flaws.

2. The method of claim 1 wherein said step of extracting the location and size data from the differential spectra is alternatively performed in accordance with at least two different operational modes dependent on the size of the flaws.

3. The method of claim 2 wherein one of the operational modes is performed in additional dependence on density of the test object and multiple scattering of the radiation.

4. The method of claim 3 including the step of incrementally displacing the test object relative to said source until the beam of radiation therefrom intersects the test object before said step of extracting location and size data is performed.

5. In a system for non-destructive examination of a test object by irradiation thereof from a monoenergetic source emitting a collimated beam of radiation and detection of scattered radiation emerging from the irradiated test object within a measurement field to provide scattered radiation density distribution profiles of the field from measurement of energy levels therein, a method of analyzing the detection of flaws in said irradiated test object, including the steps of: comparing the radiation density distribution profiles with a reference profile corresponding to measured energy levels of scattered radiation emerging from an irradiated flawless object to provide differential spectra of the field; determining spatial relationships of the measured energy levels in the field relative to said beam of radiation; and extracting location and size data of the flaws in the test object from the differential spectra by data transformation thereof in accordance with said determined spatial relationships, said step of extracting the location and size data of the flaws including plotting of the differential spectra as differential energy levels along an axis corresponding to that of the beam of radiation and measuring the areas under pulse portions of the plotted spectra respectively corresponding to peak values of the measured energy levels, said measured areas being substantially proportional to the size of the flaws.

* * * * *